(12) United States Patent  
Whipple

(10) Patent No.: US 9,289,311 B1  
(45) Date of Patent: Mar. 22, 2016

(54) ARTIFICIAL DISC WITH SHUNT ENHANCED MAGNETIC FIELDS

(71) Applicant: Amendia, Inc., Marietta, GA (US)

(72) Inventor: Dale Whipple, Woodstock, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/820,124

(22) Filed: Aug. 6, 2015

Related U.S. Application Data

(63) Continuation-in-part of application No. 14/737,748, filed on Jun. 12, 2015.

(51) Int. Cl.
*A61F 2/44* (2006.01)

(52) U.S. Cl.
CPC ......... *A61F 2/4425* (2013.01); *A61F 2002/448* (2013.01); *A61F 2210/009* (2013.01); *A61F 2310/00017* (2013.01); *A61F 2310/00179* (2013.01)

(58) Field of Classification Search
None
See application file for complete search history.

(56) References Cited

U.S. PATENT DOCUMENTS

2007/0233251 A1* 10/2007 Abdou ................. A61F 2/4405
623/17.11

* cited by examiner

*Primary Examiner* — Sameh Boles
(74) *Attorney, Agent, or Firm* — David L. King

(57) ABSTRACT

An improved artificial disc has a superior and inferior member. The superior member has an upper body portion and a flange portion for positioning and attachment to an upper vertebral body. The inferior member has a lower body portion and a flange portion for positioning and attachment to a lower vertebral body. The upper body portion and the lower body portions, when positioned in a disc space between the upper and lower vertebral bodies and affixed to a respective vertebral body at the flange portion, are independently movable relative to the other along complimentary bearing surfaces on each of the superior and inferior members. The complimentary bearing surfaces are self-aligned by a magnetic attraction force generated by at least one first permanent magnet in either the inferior or superior member.

7 Claims, 8 Drawing Sheets

ARTIFICIAL DISC WITH SHUNT ENHANCED MAGNETIC FIELDS

RELATED APPLICATIONS

This application is a continuation in part of U.S. Ser. No. 14/737,748 entitled "Artificial Disc" filed Jun. 12, 2015.

FIELD OF THE INVENTION

This application relates to an artificial prosthetic spinal disc or spinal implant device for replacing a damaged disc yet providing for mobility between the adjacent vertebrae. The implant device is particularly useful in the cervical portion of the spine and even lower where mobility of the vertebral bodies is desirably needed to be maintained.

BACKGROUND OF THE INVENTION

Intervertebral discs are soft and compressible. They are interposed between adjacent vertebral body elements of the spine. They act as shock absorbers for the spine, allowing it to flex, bend, and rotate. Degenerative disc disease can occur throughout the spine, but most often occurs in the discs in the lower back (lumbar region) and the neck (cervical region).

As the process of degeneration continues, micro tears or cracks occur in the outer layer (annulus fibrosus) of the disc. The jellylike material inside the disc (nucleus pulposus) may be forced out through the tears or cracks in the annulus, which causes the disc to bulge, break open (rupture), or break into fragments.

The economic impact of degenerative disc disease is enormous accounting for a significant morbidity and lost wages.

The physical properties of the disc are the nucleus pulposus which is composed of type II collagen and the annulus fibrosis which surrounds the disc and gives it significant form. The annulus composed of type I collagen. The nucleus pulposus is largely made up of molecules called proteoglycans. These proteoglycans have an affinity for water. It is this retention of water and the stoichiometry of folded molecules that is responsible for the unique mechanical properties of the disc. If these proteoglycans are depleted, the discs become more rigid and the loss of fluid results in a disc that is thinner and less compliant. Clinically this results in narrowing of the distances between the vertebral elements. This is best seen on magnetic resonance imaging. Typically discs have a bright signal on T2 pulse-weighted sequences and they are hypointense on corresponding T1 images. This is due to the high fluid content of the discs. As the disc loses fluid i.e. the loss of proteoglycans, the disc loses its water signal and becomes anhidrotic and eventually mineralizes. As a result, these individuals develop the symptoms in the spine contributable to loss of the normal disc architecture. As the process of degeneration continues, one develops micro tears or cracks and fissures in the annulus fibrosis and through these cracks and fissures the nucleus pulposus, which is largely gelatinous, may extrude. The extruded disc material may efface the dura and cause significant nerve compression which may result in traumatic neuritic pain and or motor loss.

Once the damage to the disc is so complete the ability to correct the problem is limited to artificial implants to restore the disc space. A more traditional approach was to use a spinal fusion implant that provided the spacing between the vertebral bodies, but thereafter allow bone growth to fuse the adjacent vertebrae together destroying any ability of these fused vertebrae to articulate.

More recently, cervical prosthetic discs have been proposed for the cervical repairs in particular ones that do not fuse the vertebral bodies, but instead allow a limited range of motion. These new articulating implant devices are a better choice until scientists can perfect disc tissue regeneration and natural biologic repair of the nucleus pulposus.

The present invention as described hereinafter is an improved spinal implant design that enhances mobility and articulation in a self-aligning and reliable construction.

SUMMARY OF THE INVENTION

An improved artificial disc has a superior member and an inferior member. The superior member has an upper body portion. The inferior member has a lower body portion. The upper body portion and the lower body portions, when positioned in a disc space between the upper and lower vertebral bodies and affixed to a respective vertebral body, are independently movable relative to the other along complimentary bearing surfaces on each of the superior and inferior members. The complimentary bearing surfaces are self-aligned by a magnetic attraction force generated by a permanent magnet in either the inferior or superior member; the magnet being contained in a first ferromagnetic shunt. The first ferromagnetic shunt directs the magnetic field in a region defined by an outer perimeter field boundary. The field boundary is projected to an opposed second shunt in the opposite inferior or superior member. The opposed second shunt has a concave central portion extending to a maximum thickness along an outer perimeter. The inferior or superior member with a magnet has a third ferromagnetic shunt overlying an outer surface of the magnet. The third shunt has a convex curvature complimentary to the concave central portion of the second shunt of the opposite inferior or superior member. The inferior and superior members each have a thin portion of substantially uniform thickness. One portion is concave shaped adjacent the second shunt and the other portion is domed convexly adjacent the third convex shunt wherein the distance across both portions is substantially constant above or below the respective second or third shunt. The bearing surfaces are formed at least partially by an exterior surface of each respective web.

The inferior or superior member opposite the member with the permanent magnet has the second shunt made of a ferromagnetic composition responsive to the magnetic attractive force to self-align the complimentary bearing surfaces to a null position.

The improved artificial disc further has a pair of flange portions. One flange portion on the superior member for positioning and attachment to an upper vertebral body and one flange portion on the inferior member for positioning and attachment to a lower vertebral body. The complimentary bearing surfaces can move relative to the other in any direction by a movement of the vertebral body to which the flange is fixed, the bearing surfaces will maintain an attractive magnetic field to return to contact of the bearing surfaces upon separation during said movement. Preferably, the bearing surfaces include one convex surface and one complimentary concave surface and wherein the surfaces are translatable about the other. One or both of the bearing surfaces are made of a ceramic material.

BRIEF DESCRIPTION OF THE DRAWINGS

The invention will be described by way of example and with reference to the accompanying drawings in which.

DETAILED DESCRIPTION OF THE INVENTION

Figure 1:
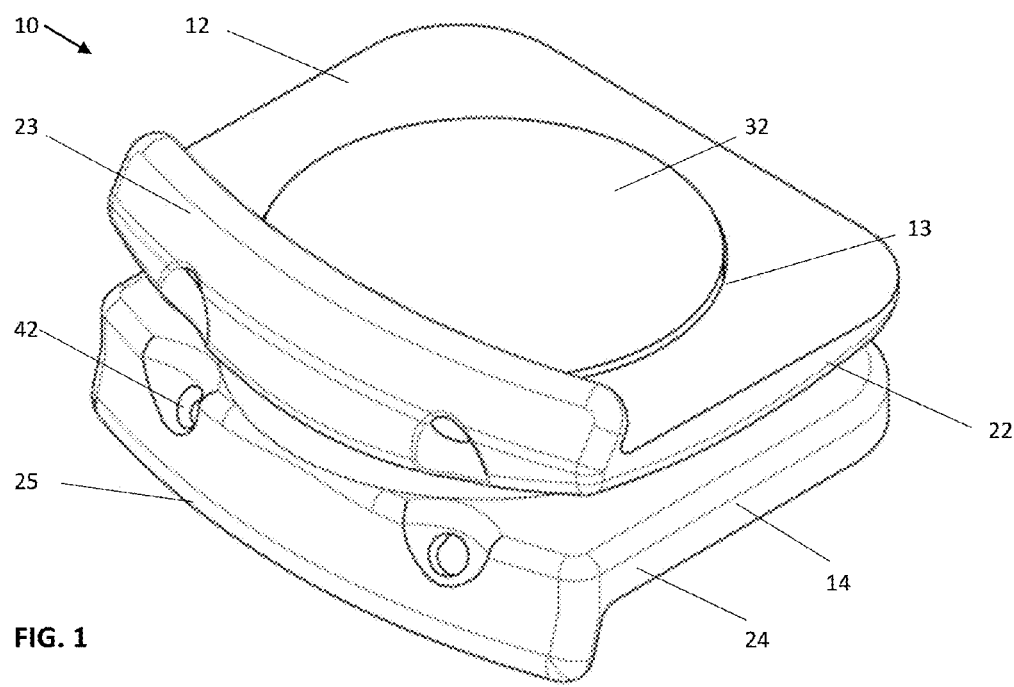
FIG. 1 is a perspective view of the implant device of the present invention.

With reference to FIGS. 1-5, a first embodiment of the present invention is illustrated. The first embodiment of the invention is an improved artificial disc assembly 10. The disc assembly 10 has a superior member 12 and an inferior member 14. The superior member 12 being configured to be attached into a disc space into an upper vertebral body. The inferior member 14 being configured to be attached into a disc space into a lower vertebral body between the two adjacent vertebral bodies. The implant 10 has main body portions 22, 24 that occupy the disc space and flange portions 23, 25 that position and allow for attachment to either the respective upper vertebral body or the lower vertebral body.

As shown, through holes 42 are provided through which the fasteners (not illustrated) can be positioned to securely attach the superior member 12 or inferior member 14 to the vertebral body to which it is to be attached. As shown, the superior member 12 has a main body portion 22 and a flange portion 23 and the inferior member 14 has a main body portion 24 and a flange portion 25. The respective through holes 42 on each side of the respective flange 23, 25 allow for the attachment of the artificial disc assembly 10 to the vertebral body to which it is to be attached.

Figure 2:
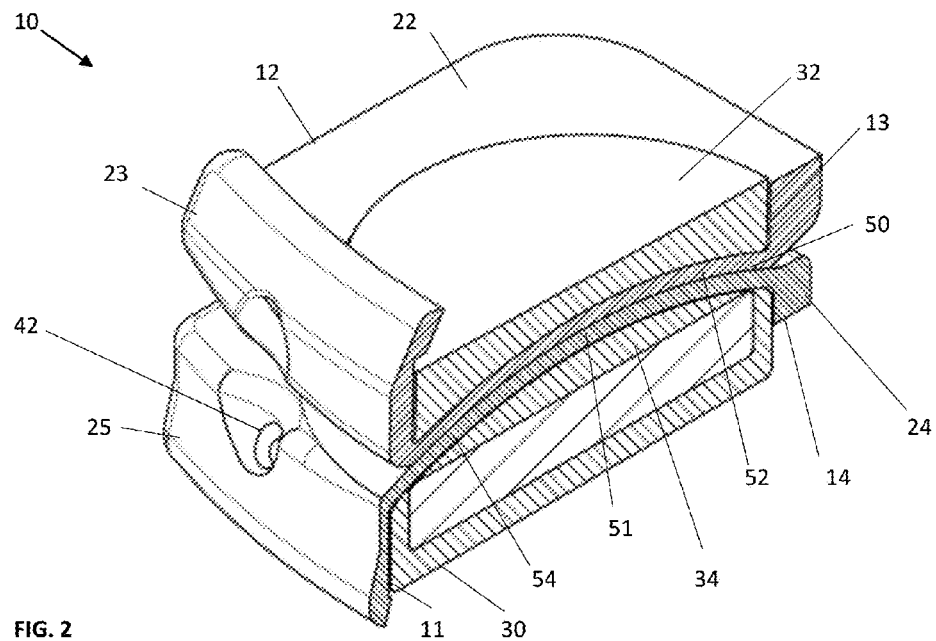
FIG. 2 is a cross-sectional perspective view of the implant device of FIG. 1.
Figure 3:
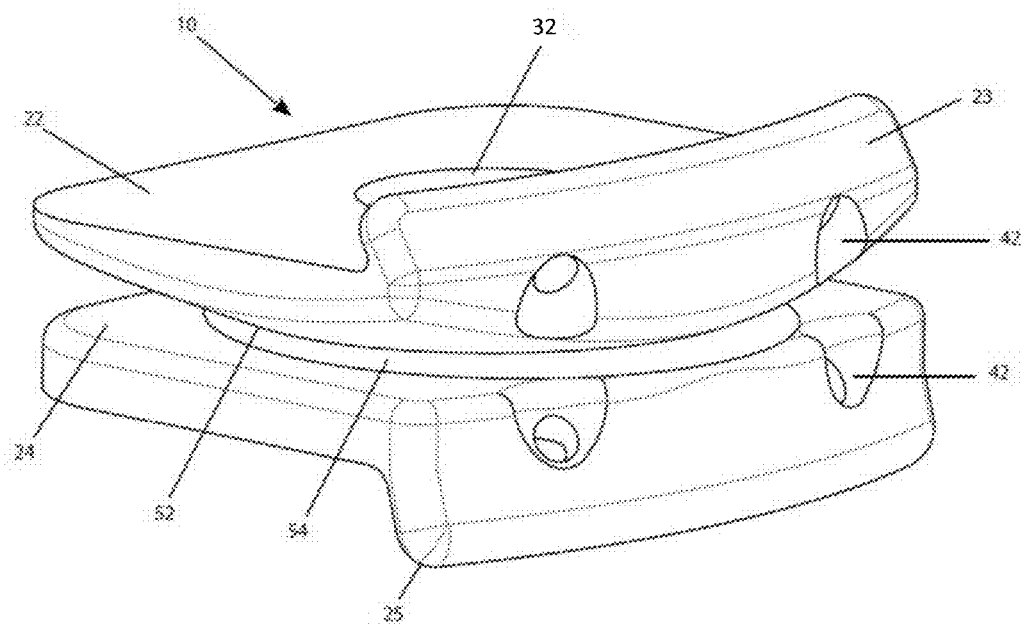
FIG. 3 is a second perspective view of the implant device of FIG. 1.
Figure 4A:
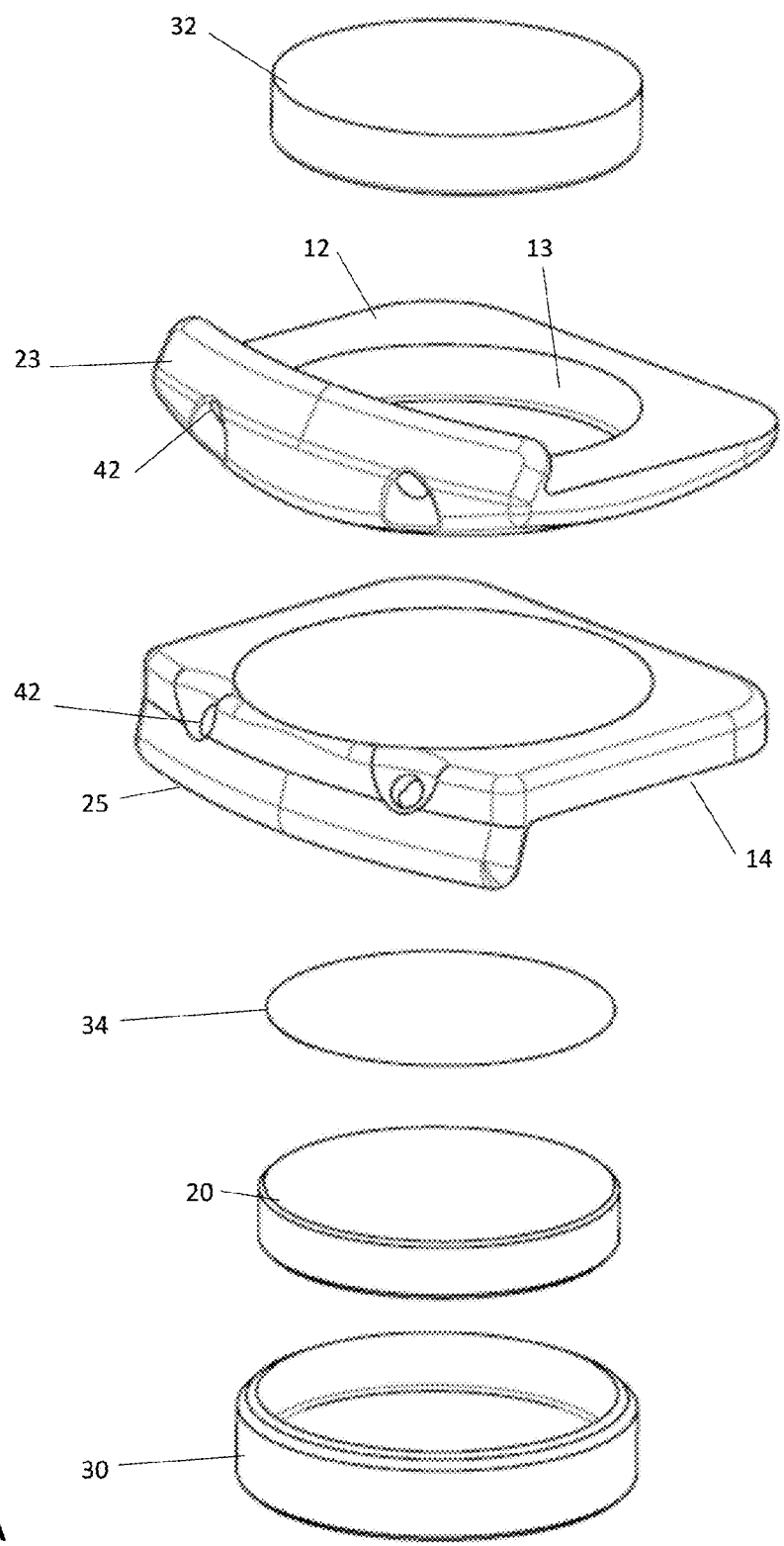
FIG. 4A is an exploded perspective top view of the implant device shown in FIG. 1.
Figure 4B:
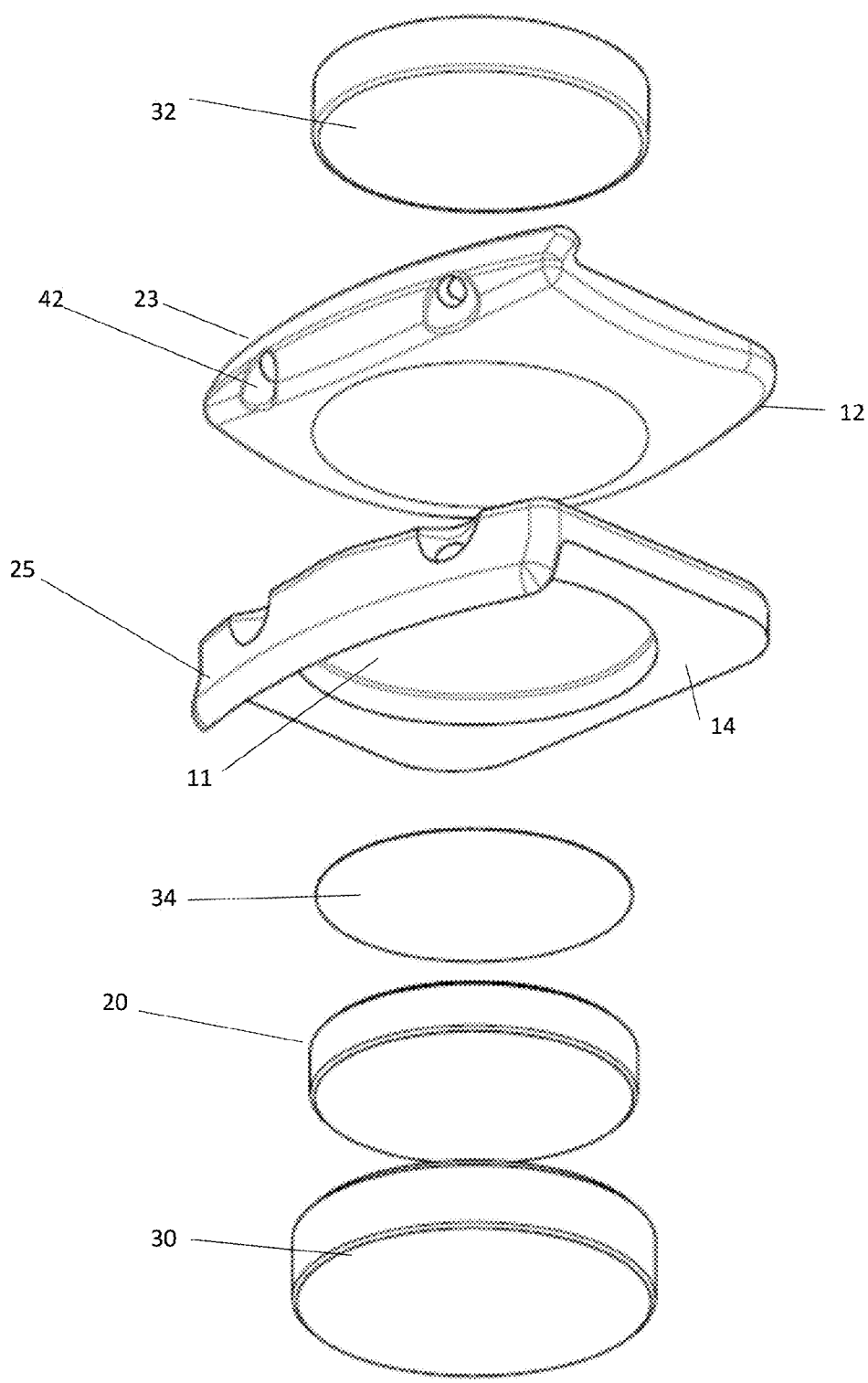
FIG. 4B is an exploded perspective bottom view of the implant device shown in FIG. 1.
Figure 4C:
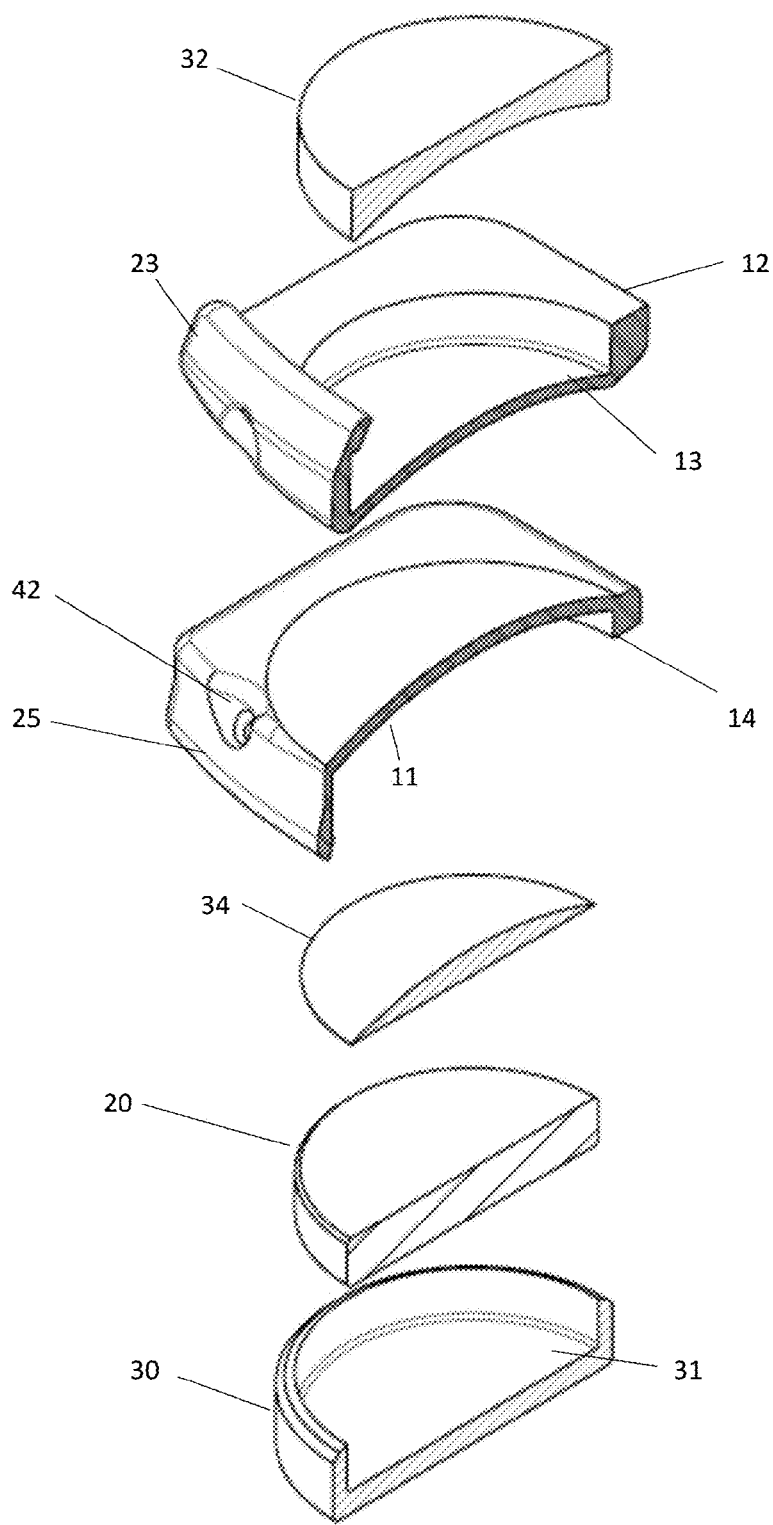
FIG. 4C is an exploded section view of the device shown in FIG. 4A.
Figure 5:
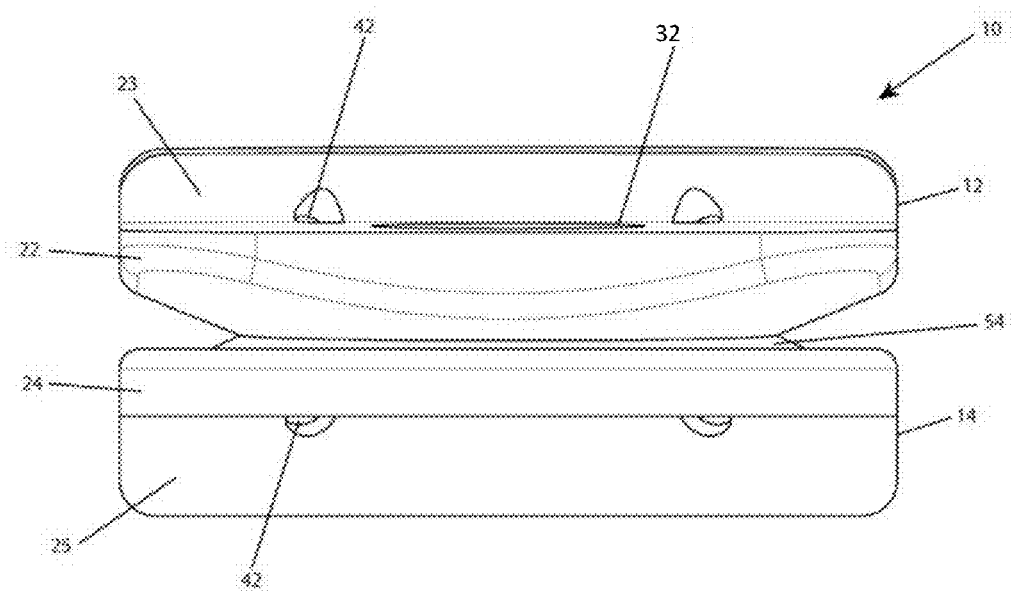
FIG. 5 is a plan view of the implant device of FIG. 1.
Figure 7:
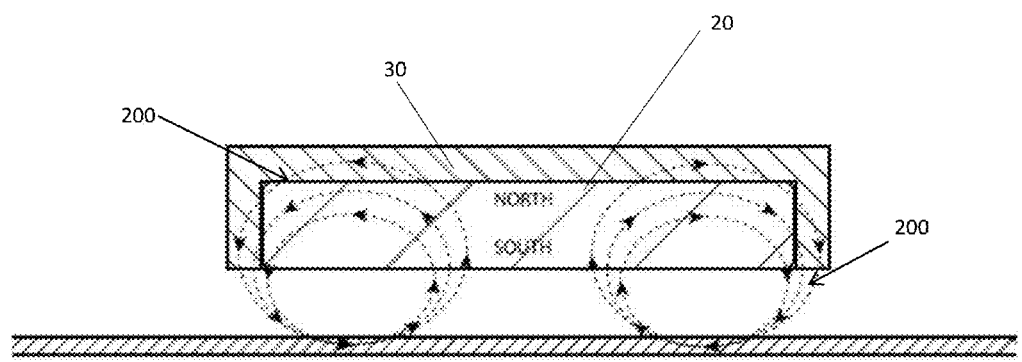
FIG. 7 is a magnet inside a first shunt showing how the magnetic field is projected out directionally bounded by the outer perimeter of the first shunt.

As shown, on the top surface of the superior member 12 is illustrated a second shunt 32, this shunt 32 can be embedded into an opening or cavity 13, as illustrated. The cross sectional view of FIG. 2 shows that both the superior member 12 and inferior member 14 where the inferior member 14 has a cavity or opening 11 for receiving a permanent magnet 20 held in a cavity or opening 31 of a first shunt 30 embedded therein and the superior member 12 has a second shunt 32. The magnet 20 shown as a round disk positioned approximately midway on one of the main body portions 22 or 24 of the member 12 or 14 and it is aligned with the second shunt 32 at an apex 51 of a bearing surface 50. The bearing surfaces 50 have the superior member 12 with a concave portion 52 and the inferior member 14 with a convex portion 54 that provides for the ability of the superior 12 and inferior 14 members to move relative to each other with regard to the complimentary shape of the bearing surfaces 50 of each portion 52, 54. The artificial disc 10 is an assembly made of these two main members 12, 14 and these parts are independent, completely separate of each other overlapping at bearing surfaces 50 coupled by the attractive forces created by the permanent magnet 20. The magnet 20, as shown in FIG. 7, has a North (N) and South (S) polarity so when assembled in the shunt 30, the magnet 20 has the south polarity surface (S) opposite the north polarity surface (N). The shunts 30, 32 and 34 insure enhanced magnetic attraction forces are generated and when in close proximity these forces are quite strong. Whichever, one or the other of the superior or inferior members 12, 14 can have the first shunt 30 holding the permanent magnet 20. The other will have the second shunt 32 with ferromagnetic material which is responsive to magnetic fields in such a way that it can be attracted to the first permanent magnet 20 in either the superior 12 or inferior 14 member. When so constructed, it is possible for the two parts when attached to the vertebral body to open and close upon movement, for example during a cervical spine procedure, the movement of the vertebral bodies can cause the implant 10 to want to open and separate. When this occurs, through movement of the neck, the implant 10 can form a gap along the bearing surfaces 50. This gap is closed upon a relaxation of the neck from the moved positon in such a fashion that the artificial disc implant 10 always wants to remain in the full contact position along the bearing surfaces 50 as the attractive forces pull the two parts 12, 14 together under any condition. Additionally, as shown in FIGS. 1, 2, 3 and 4A, 4B, 4C the artificial disc 10 may have the convex portion 52 aligned with the concave portion 54 in such a fashion that the two are matingly engaged along their respective bearing surfaces 50. It is possible that one could rotate members 12, 14 180 degrees and have the convex surface be the upper portion and the concavity be the lower portion if so desired depending on the procedure and the location where the artificial disc 10 is to be installed.

Figure 6:
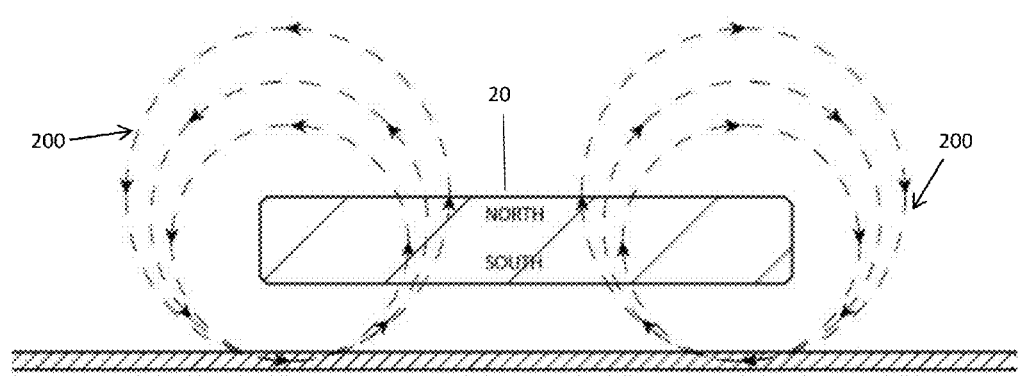
FIG. 6 is a schematic view of a magnet with no shunt to direct a magnetic field.

With reference to FIG. 6, a permanent exemplary disk magnet 20 when simply placed over a magnetically attractable plate 2 has the magnetic fields 200 radiate as shown. In the present invention, when the magnet 20 is held in the first shunt 30, as shown, the magnetic fields 200 are constrained inside the perimeter of the first shunt 30 and thus radiate projected within a directed and confined boundary, as shown in FIG. 7.

Figure 8:
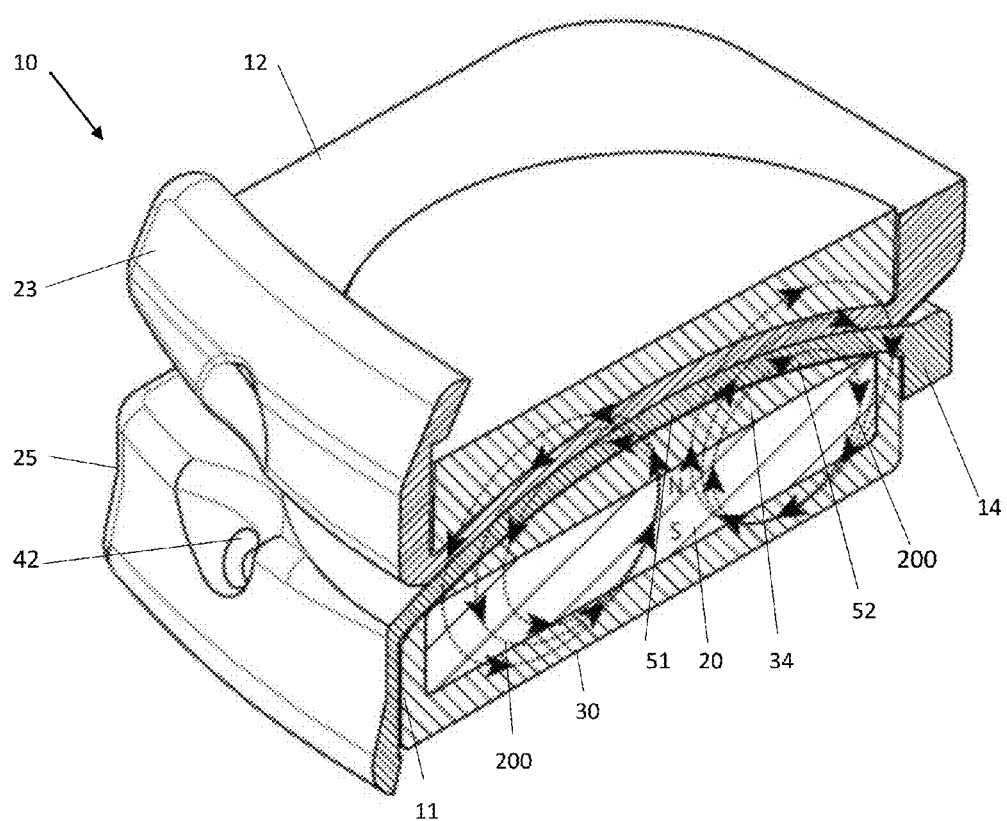
FIG. 8 shows a cross section of the device of the present invention with the shunt directed magnetic field illustrated.

As shown in FIG. 8, the magnetic fields 200 are enhanced by the convex third shunt 34 under the thin convex portion 54 of the inferior member 14 being closely spaced and nested inside the concave portion 52 of superior member 12. As shown, each portion 52, 54 has a narrow and constant thickness so the attractive forces are not only directed by the shunt 30, but enhanced by the complimentary surfaces of the shunt 32 and 34. This magnetic field enhancement is so great, one magnet 20 when used with the shunts 30, 32 and 34 has more attractive force than two unenhanced magnets without shunts. This is believed to be created by the directional field boundary created by the shunt 30 and the close proximity of the shunts 32 and 34.

In a preferred embodiment, the members 12, 14 can be made at least along one or both bearing surfaces 50 of a ceramic material for its good wear characteristics. Other parts can be made of a synthetic polymer, either with or without ferromagnetic particles or properties. As shown, the convex and concave portions are of a hemispherical or partial hemispherical shape employing a constant radius of curvature. Other shapes employing variations of radius or multiple radii are contemplated as suitable alternatives.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An improved artificial disc comprises: a superior member having an upper body portion; an inferior member having a lower body portion; and wherein the upper body portion and the lower body portions, when positioned in a disc space between the upper and lower vertebral bodies and affixed to a respective vertebral body, are independently movable relative to the other along complimentary bearing surfaces on each of the superior and inferior members and wherein the complimentary bearing surfaces are self-aligned by a magnetic attraction force generated by a permanent magnet in either the inferior or superior member; the magnet being contained in a first ferromagnetic shunt for directing the magnetic field in a region defined by an outer perimeter field boundary, the field boundary being projected to an opposed second shunt in the opposite inferior or superior member, wherein the opposed second shunt has a concave central portion extending to a maximum thickness along an outer perimeter, and wherein the inferior or superior member with a magnet has a third ferromagnetic shunt overlying an outer surface of the magnet, the third shunt has a convex curvature complimentary to the concave central portion of the opposite inferior or superior member.

2. The improved artificial disc of claim 1 wherein the inferior and superior members each have a thin portion of substantially uniform thickness, one portion being concave shaped adjacent the second shunt and one portion being domed convexly adjacent the third convex shunt wherein the distance across both portions is substantially constant above or below the respective second or third shunt.

3. The improved artificial disc of claim 2 wherein the bearing surfaces are formed at least partially by an exterior surface of each respective portion.

4. The improved artificial disc of claim 1 wherein the inferior or superior member opposite the member with the first permanent magnet has the second shunt made of a ferromagnetic composition responsive to the magnetic attractive force to self-align the complimentary bearing surfaces to a null position.

5. The improved artificial disc of claim 1 further comprises;
a pair of flange portions, one flange portion on the superior member for positioning and attachment to an upper vertebral body and one flange portion on the inferior member for positioning and attachment to a lower vertebral body; and
wherein the complimentary bearing surfaces can move relative to the other in any direction by a movement of the vertebral body to which the flange is fixed, the bearing surfaces will maintain an attractive magnetic field to return to contact of the bearing surfaces upon separation during said movement.

6. The improved artificial disc of claim 1 wherein the bearing surfaces include one convex surface and one complimentary concave surface and wherein the surfaces are translatable about the other.

7. The improved artificial disc of claim 1 wherein one or both of the bearing surfaces are made of a ceramic material.

* * * * *